(12) United States Patent
Basham (10) Patent No.: US 11,360,067 B2
(45) Date of Patent: Jun. 14, 2022

(54) PORTABLE FLUE GAS ANALYSER

(71) Applicant: Crowcon Detection Instruments Limited, Abingdon (GB)

(72) Inventor: Paul Basham, Abingdon (GB)

(73) Assignee: Crowcon Detection Instruments Limited, Abingdon (GB)

( * ) Notice: Subject to any disclaimer, the term of this patent is extended or adjusted under 35 U.S.C. 154(b) by 650 days.

(21) Appl. No.: 16/394,382

(22) Filed: Apr. 25, 2019

(65) Prior Publication Data

US 2019/0331339 A1 Oct. 31, 2019

(30) Foreign Application Priority Data

Apr. 25, 2018 (GB) .................................. 1806769

(51) Int. Cl.
| | |
|---|---|
| *G01N 33/00* | (2006.01) |
| *F23N 5/24* | (2006.01) |
| *F23N 5/00* | (2006.01) |
| *G01N 33/22* | (2006.01) |
| *F23N 5/18* | (2006.01) |

(52) U.S. Cl.
CPC ......... *G01N 33/0031* (2013.01); *F23N 5/003* (2013.01); *F23N 5/24* (2013.01); *G01N 33/004* (2013.01); *G01N 33/0047* (2013.01); *G01N 33/225* (2013.01); *F23N 2005/185* (2013.01); *F23N 2223/08* (2020.01); *F23N 2223/10* (2020.01); *F23N 2235/02* (2020.01); *F23N 2235/12* (2020.01); *F23N 2239/04* (2020.01); *F23N 2900/05001* (2013.01); *F23N 2900/05002* (2013.01)

(58) Field of Classification Search
CPC ............ G01N 33/0031; G01N 33/004; G01N 33/0047; G01N 33/225; F23N 5/003; F23N 2223/08; F23N 2223/10; F23N 2239/04; F23N 2900/05001; F23N 2900/05002
See application file for complete search history.

(56) References Cited

U.S. PATENT DOCUMENTS

| | | | | |
|---|---|---|---|---|
| 4,408,569 | A * | 10/1983 | Novak | ..................... F23N 5/006 |
| | | | | 122/448.1 |
| 5,599,179 | A * | 2/1997 | Lindner | ................... F23N 5/082 |
| | | | | 431/12 |
| 2010/0028819 | A1 * | 2/2010 | Knittel | .................... F23N 5/003 |
| | | | | 431/76 |

FOREIGN PATENT DOCUMENTS

WO WO-2020025758 A1 * 2/2020 ............. F22B 35/00

* cited by examiner

*Primary Examiner* — Benjamin R Schmitt
(74) *Attorney, Agent, or Firm* — Brient IP Law, LLC (57) ABSTRACT

A flue gas analyser for determining the efficiency of a burner burning a supply gas and producing a flue gas by: calculating an efficiency of the burner based on a detected amount of a first target gas in the flue gas and an expected amount of the first target gas in the flue gas; predicting an amount of a second target gas in the flue gas based on the efficiency of the burner; estimating a composition of the supply gas based on a detected amount of the second target gas in the flue gas and the predicted amount of the second target gas in the flue gas; and correcting the calculated efficiency of the burner based on the estimated composition of the supply gas.

17 Claims, 3 Drawing Sheets

Figure 1

PORTABLE FLUE GAS ANALYSER

CROSS REFERENCE TO RELATED APPLICATIONS

This application claims priority to GB Patent Application Serial No. 1806769.4, filed Apr. 25, 2018, entitled "A Portable Flue Gas Analyser," the disclosure of which is hereby incorporated by reference in its entirety.

TECHNICAL FIELD

Various embodiments of the present invention relate to a method and apparatus for estimating the efficiency of a burner, such as a domestic boiler, by analysing the flue gas of the burner. Specifically, various embodiments enable the determination of the composition of the gas being burned and, based on the determined composition of the gas, the calculation of an efficiency of the burner.

BACKGROUND

It is known that measuring the efficiency of a boiler, for example a domestic water heater, is an important factor when seeking to decide whether a boiler needs replacing. A large proportion of household spending is spent on heating bills, and as such, the correct estimation of a boiler's efficiency can have a direct impact on reducing the amount spent on heating. Moreover, many countries have various boiler efficiency regulations, such as the UK's Boiler (Efficiency) Regulations 1993, which introduce requirements with regards a boiler's efficiency rating.

The efficiency of a boiler may be measured in a number of known ways. The thermal efficiency of a boiler relates to the heat exchange efficiency of the boiler. That is, the effectiveness of the heat exchanger at transferring the heat energy from the combustion process to the water in the boiler. The direct calculation of the thermal efficiency of a boiler requires the calculation or estimation of many parameters including the calorific value of the fuel, the amount of steam generated, and enthalpy of the steam and water. As such, direct thermal efficiency methods require precise measurements that may be difficult to obtain accurately in a non-invasive way within a boiler system.

Combustion efficiency is an alternative means of measuring the efficiency of a boiler which measures the ability of the burner of a boiler to burn fuel. The composition of the exhaust gas measured in the flue, namely the amount of unburnt fuel and the amount of oxygen in the exhaust gas, are used to estimate the combustion efficiency of the burner. As such, estimating the combustion efficiency of a burner requires fewer measurements than thermal efficiency; specifically, measuring the exhaust gases present in the flue.

When estimating the combustion efficiency of the burner, the type of fuel being burnt needs to be known in order to correctly calculate the efficiency. A domestic boiler may burn various different fuels such as coal, oil, and gas. Domestic gas supplies include propane, butane, and methane. Generally, methane is the main gaseous fuel.

Biogas is a clean energy alternative fuel to standard domestic gas supplies. It is known that biogases are a clean and environmentally friendly fuel that can be used as a supply fuel for a boiler. Biogas is a green energy source that can be sourced from all biogenic wastes such as sewage, agricultural waste, and household waste. The chemical composition of raw biogas is typically a mixture of methane ($CH_4$) and carbon dioxide ($CO_2$) with other trace gases such as nitrogen ($N_2$), hydrogen ($H_2$), and oxygen ($O_2$). Although biogas is a naturally occurring fuel source, carbon dioxide ($CO_2$) may be added to biogas by the fuel supplier. As such, the relative percentages of the composite gases may vary, making the calculation of the burner efficiency difficult to measure accurately. For example, when estimating the combustion efficiency of a burner, the presence of carbon dioxide ($CO_2$) in the exhaust gas may be related to unburnt fuel due to the $CO_2$ concentration varying within the fuel supply, or as a result of the combustion process. This uncertainty can lead to a less accurate determination of the efficiency of the burner.

There are several known flue gas analysers that are commercially available. These analysers are able to detect amounts of different gases in a boiler's flue. Some analysers may further provide estimation of the efficiency of a boiler based on the detected amount of flue gases. Existing flue gas analysers used to measure combustion efficiency are able to detect the presence of this $CO_2$ in the exhaust gas, however such systems are unable to compensate the efficiency estimation based on the fuel composition.

An object of various embodiments of the invention is to produce a portable flue gas analyser that provides accurate estimates of the efficiency of boilers using a range of different supply gas types with different fuel compositions. The flue gas analyser comprises: one or more gas detectors to detect the amount of different gases in the flue of a boiler, and electronics enabled to determine the fuel efficiency of the burner using the measurements.

According to one embodiment of the invention, there is provided a flue gas analyser for determining the efficiency of a burner burning a supply gas and producing a flue gas, comprising: a first gas detector, configured to detect an amount of a first target gas in the flue gas; a second gas detector, configured to detect an amount of a second different target gas in the flue gas; and a processing means (e.g., a computer processor); wherein the processing means is configured to: calculate an efficiency of the burner based on the detected amount of the first target gas in the flue gas and an expected amount of the first target gas in the flue gas; predict an amount of the second target gas in the flue gas based on the efficiency of the burner; estimate a composition of the supply gas based on the detected amount of the second target gas in the flue gas and the predicted amount of the second target gas in the flue gas; and correct the calculated efficiency of the burner based on the estimated composition of the supply gas.

According to a further aspect of various embodiments of the invention, there is provided a method of using a flue gas analyser to determine the efficiency of a burner burning a supply gas and producing a flue gas, the method comprising the steps of: measuring an amount of a first target gas in the flue gas; estimating an efficiency of the burner based on an expected amount of the first target gas in the flue gas and the measured amount of the first target gas in the flue gas; adjusting the estimated efficiency of the burner; wherein the adjusting comprises the steps of: predicting an amount of a second target gas in the flue gas using the estimated efficiency of the burner; measuring an amount of the second target gas in the flue gas; comparing the predicted amount of the second target gas in the flue gas with the measured amount of the second target gas in the flue gas to obtain a correction factor for the second target gas in the flue gas; determining a predicted fuel composition of the supply gas using the correction factor for the second target gas in the flue gas; and correcting the estimated efficiency of the burner using the predicted fuel composition of the supply gas.

According to an additional aspect of the invention, there is provided a flue gas analyser system, comprising: a supply connector, configured to connect to a supply gas; a burner, connected to the supply connector and configured to burn the supply gas and produce a flue gas; a flue element, connected to the burner and configured to convey the flue gas of the burner; and a flue gas analyser according to claim 1, wherein the first gas detector and the second gas detector are positioned such that they detect a first target gas in the flue gas conveyed in the flue element and a second target gas in the flue gas conveyed in the flue element.

Such aspects provide for a more accurate flue gas analyser whereby the composition of the supply gas is compensated for without the need to know the exact proportion of gases within the supply gas. More accurate estimations as to the efficiency of a boiler therefore provide for reductions in cost for the owner of a boiler since less efficient boilers may be identified and replaced. Additionally, more accurate estimations as to the efficiency of a boiler reduce the likelihood of needlessly replacing a boiler thereby reducing the likelihood of additional cost spent by a user. In addition, such aspects provide for a flue gas analyser that is simpler to operate since there is no need for the supply fuel to be entered and determined manually. Furthermore, such aspects provide for a flue gas analyser which is simpler to update to allow for new and/or additional supply fuels to be compensated for.

Optionally but preferably, there is provided a flue gas analyser wherein the processor is further configured to determine the expected amount of the first target gas in the flue gas using a supply gas profile of the supply gas; preferably wherein the flue gas analyser is associated with one or more look up tables and/or databases comprising information on the supply gas profile for at least one of a number of supply gases; preferably wherein the supply gas profile comprises a ratio value for one of an at least one of a number of supply gases, wherein the ratio value is the ratio of an amount of a first target gas with respect to an amount of a second target gas; preferably wherein the supply gas profile comprises an expected amount of a first target gas; preferably wherein the supply gas profile comprises an expected amount of a second target gas.

Beneficially, this provides for the flue gas analyser to be used in a range of settings and the same flue gas analyser may be used for different supply fuel types. Therefore, the flue gas analyser provides for a more efficient and simpler means of accurately estimating the efficiency of a boiler.

Optionally but preferably, there is provided a flue gas analyser wherein the processor is further configured to obtain the supply gas profile of the supply gas by matching the ratio value of the detected amount of the first target gas in the flue gas with respect to the detected amount of the second target gas in the flue gas to a corresponding ratio value in the supply gas profile in the one or one or more look up tables and/or databases comprising information on the supply gas profile. Beneficially, this allows the flue gas analyser to be used in a range of different setting and the same flue gas analyser can be used for different supply fuel types. Furthermore, the flue gas analyser may be configured to predict new supply fuel types by amending the one or more look up tables and/or databases. This provides a simple and cost effective means of updating and upgrading a flue gas analyser.

Optionally but preferably, there is provided a flue gas analyser wherein the supply gas is a biogas comprising a mixture of $CO_2$ and $CH_4$. Beneficially, such biogases are a clean and renewable source of energy. Furthermore, biogas production is carbon neutral and does not contribute to greenhouse gas emissions.

Optionally but preferably, there is provided a flue gas analyser wherein the supply gas is a mixture of methane and hydrogen. Beneficially, such biogases are a clean and renewable source of energy. Furthermore, biogas production is carbon neutral and does not contribute to greenhouse gas emissions.

Optionally but preferably, there is provided a flue gas analyser wherein the first target gas is $O_2$ and the first target gas detector is configured to detect $O_2$; and wherein the second target gas is $CO_2$ and the second target gas detector is configured to detect $CO_2$. Beneficially, the detection of oxygen and carbon dioxide in the exhaust gas allows the efficiency of the boiler to be estimated.

Optionally but preferably, there is provided a flue gas analyser wherein the flue gas analyser comprises a power source configured to connect to power one or more of the processor, first target gas detector, and second target gas detector. In an example, the power source may comprise a removable and replaceable battery cell. In further examples, the power source may comprise a rechargeable power source such as a rechargeable battery cell. In yet another example, the power source may comprise an energy harvesting means configured to obtain energy from the environment such as a solar panel.

Optionally but preferably, there is provided a flue gas analyser wherein the processing means is a computer processor. Such a computer processor may be a micro-controller such as is known in the art.

Further aspects of various embodiments of the invention are apparent from the appended claim set.

BRIEF DESCRIPTION OF DRAWINGS

Embodiments of the invention will now be described with reference to the accompanying drawings, in which.

DETAILED DESCRIPTION

An embodiment of the present invention will now be described with reference to the attached figures. It is to be noted that the following description is merely used for enabling the skilled person to understand the present invention, without any intention to limit the applicability of the present invention to other embodiments which could be readily understood and/or envisaged by the reader. In particular, the present invention is described in relation to gas burners, such as a domestic boilers. However, it will be appreciated that the present invention could be applied in other areas such as handheld devices for gas monitoring other burners, for example, industrial and commercial boilers. Furthermore, whilst the device is taught with specific reference to a handheld device the techniques described herein may be utilised for other forms of device, such as mounted devices.

It is noted that a discussion of a preferred embodiment is provided below. It should be understood that this discussion is provided as a particular example of various embodiments of the invention and that this patent application may include claims that cover this particular embodiment and/or others that may not. Accordingly, no assumption should be made that all of the application's claims cover the preferred embodiment.

Figure 1:
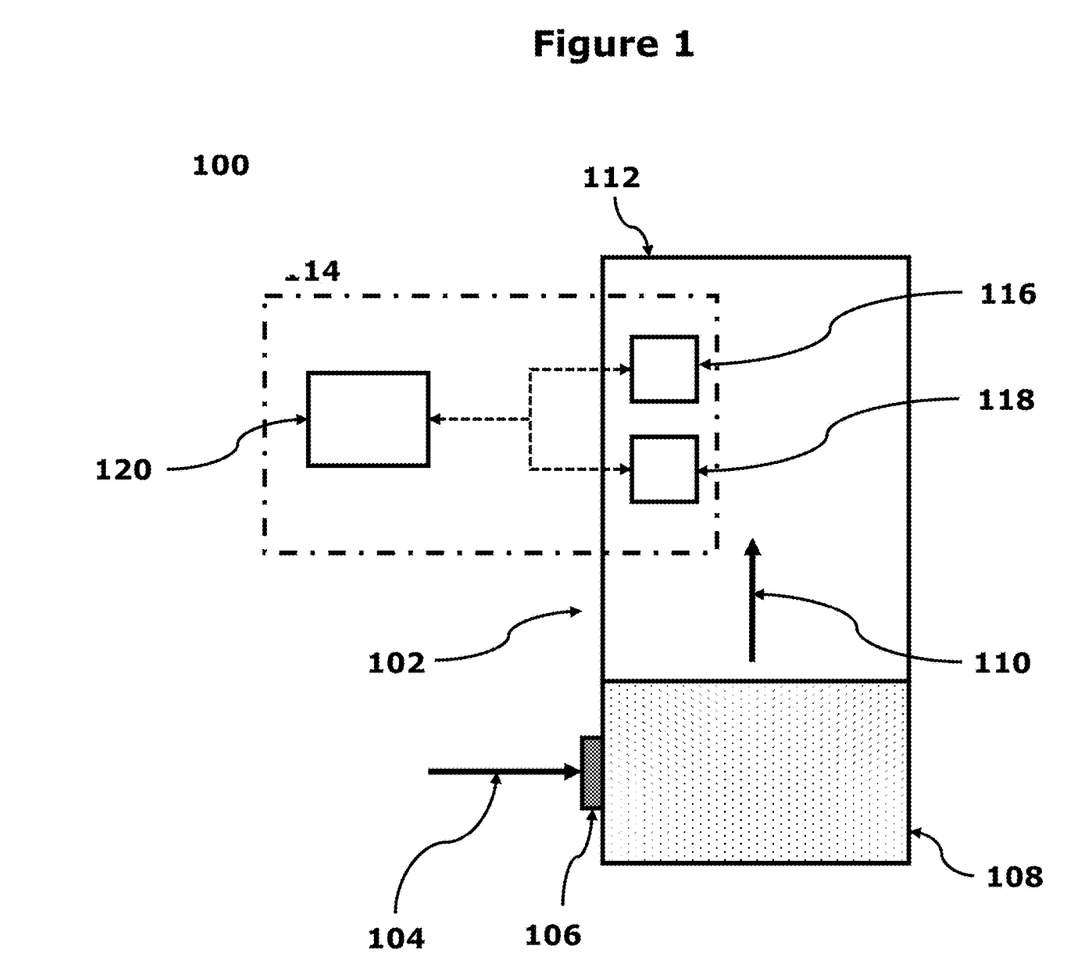
FIG. 1 shows a schematic of a flue gas analyser system for estimating the efficiency of a boiler according to a preferred embodiment.

FIG. 1 shows a schematic of a flue gas analyser system 100 which is configured to estimate the efficiency of a boiler according to a preferred embodiment. The figure shows: a boiler 102, a supply gas 104, a supply gas connector 106, a burner 108, a flue gas 110, a flue 112, and a flue gas analyser 114 comprising: a first gas detector 116, a second gas detector 118, and a processor 120. The flue gas analyser 114 may also comprise features which are commonly associated with a flue gas analyser 114 such as a memory, a power source, display, and housing (these are not shown for ease of understanding). The boiler 102 is any known suitable boiler 102, for example a commercially available boiler 102 used in a domestic or commercial environment. The boiler 102 is connected to the supply 104 via the connector 106 in a known manner. The supply gas 104 is burned in the burner 108 in a known manner. The supply gas 104 in an example comprises a biogas which has an unknown composition. In further examples the supply gas 104 is butane, or other types of fuel such as coal, oil etc.

Various embodiments of the present invention are related to the flue gas analyser 114, which is configured to estimate the efficiency of the burner 108 by detecting an amount of a first and second gas in the exhaust gas 110 produced as a result of combustion 110. The flue gas analyser 114 can further estimate the composition of the supply gas 104 provided to the burner. A more accurate estimation of the efficiency of the burner 108 is given by adjusting the estimated efficiency based on the calculated composition of the supply gas 104. It is desirable to be able to adjust the efficiency in such a way since the amount of the first gas and second gas detected in the flue gas may be affected by both the combustion process and the composition of the supply gas. Furthermore, it is desirable to have more accurate estimation of burner efficiency in order to detect inefficiencies in the boiler. Improving such inefficiencies may lead to more efficient use of natural resources, and savings in money due to less supply gas being used during the combustion process. The process through which the composition of the supply gas 104 and the efficiency of the burner 108 is determined is described in detail below.

The boiler 102 of the flue gas analyser system 100 takes in a supply gas 104, through the gas supply connector 106, in order to combust the supply gas in the burner 108. In the preferred embodiment, the boiler 102 is a domestic boiler used to generate heat for use in heating a water supply (not shown). Alternatively, the boiler 102 may be a commercial boiler or an industrial boiler. The gas supply connector 106 may be formed as part of a boiler or may be a separate component. The gas supply connector 106 may further comprise a valve in order to turn on or off the gas supply to the boiler.

The supply gas 104 may be any form of combustible gas. In the preferred embodiment, the supply gas 104 is a biogas which contains a mixture of methane ($CH_4$) and carbon-dioxide ($CO_2$). As such, a biogas may be thought of as being primarily composed of a proportion of $CH_4$ and a proportion of $CO_2$, along with a small proportion of trace gases such as nitrogen ($N_2$), hydrogen ($H_2$), oxygen ($O_2$), and hydrogen sulfide ($H_2S$).

Advantageously, biogases are a clean and renewable energy source. Furthermore, biogas production is carbon neutral and does not contribute to greenhouse gas emissions. However, the proportion of $CO_2$ present in a biogas may change between different types of gas supply. In the preferred embodiment, a typical biogas supply is considered to contain approximately 60% $CH_4$ and 40% $CO_2$. However, a biogas' mixture may vary and contain in the range of 50-75% $CH_4$ and 25-50% $CO_2$.

When burning a supply gas 104, such as a biogas, in the burner 108, the combustion process carried out in the burner 108 produces exhaust gas 110. An exhaust gas 110 will typically contain a mixture of products produced as a result of combustion, as well as an amount of unburnt fuel. The exhaust gas can be used to measure the combustion efficiency of a burner.

Combustion will typically produce a proportion of carbon dioxide ($CO_2$) and a proportion of oxygen ($O_2$). Other gases such as carbon monoxide (CO) and nitrogen ($N_2$) may also be present.

The composition of the exhaust gas 110 will change depending on both the efficiency of the burner 108, and the type of supply gas 104 used. As an example, the proportion of oxygen ($O_2$) in the exhaust gas 110 may depend upon the efficiency of the burner 108 as it may indicate that more oxygen ($O_2$), i.e. excess air, was provided to the burner 108 than was needed in the combustion process. The proportion of carbon dioxide ($CO_2$) in the exhaust gas 110 is a further indication of fuel efficiency. Carbon dioxide ($CO_2$) is a combustion product and each fuel supply type has a maximum amount of $CO_2$ that can be converted as a result of combustion. The amount of carbon dioxide measured in the exhaust gas 110 can be compared to this maximum amount for a given fuel to determine the efficiency of the burner.

Increasing oxygen supplied to the burner has the benefit of ensuring complete combustion, that is all hydrogen and carbon in the fuel are oxidized to water ($H_2O$) and carbon dioxide ($CO_2$). However, for maximum combustion efficiency, low excess air is desirable.

Different compositions of biogas, as described above, will produce different proportions of gases within the exhaust gas 110. As an example, a supply gas 104 of biogas with a higher proportion of carbon dioxide ($CO_2$) may lead to a higher proportion of $CO_2$ in the exhaust gas 110. This increased $CO_2$ is a product of the type of supply gas 104 as opposed to the combustion process.

The amount of $CO_2$ in the supply gas may vary when using a biogas as a supply gas. In some embodiments the amount of variation may be 5%, in further embodiments the amount of variation is dependent on the location with a variation of up to 4.5%, or 6.5%, within 3 miles of a gas terminal being allowed. As such, the calculations of expected levels of $O_2$ and $CO_2$, as required for the estimation of burner efficiency, will change.

Therefore, although the composition of the exhaust gas 110 can be used to estimate the efficiency of a burner 108, the presence of certain gases may be a result of the composition of the supply gas as opposed to the combustion process. An aspect of various embodiments of the claimed invention, as described in more detail below, is that a more accurate estimation of the efficiency of a burner is given by compensating for the gases detected in the flue gas 110 that are a product of the composition of the supply gas 104, as opposed to the products of combustion.

Referring once again to FIG. 1, the boiler 102 has a flue 112 which is connected to the burner 108 in order to channel the exhaust gas 110 away from the burner 108. The exhaust gas 110 may also be referred to as flue gas.

The flue 112 acts as a chimney in order to expel the flue gas 110 away from the burner. Typically, the flue 112 will contain at least two openings (not shown), one of which connects the flue 112 to the burner 108, and the other of which acts as a vent from which the flue gas 110 is expelled.

A flue gas analyser 114 is used to measure the presence of certain gases within the flue gas 110 of the flue 112, and estimate the efficiency of the burner 108. In the preferred embodiment, the flue gas analyser 114 has a first gas detector 116 and a second gas detector 118 which are positioned relative to the flue 112 such that they can measure an amount of a first gas and second gas within the flue gas 110. In an alternative embodiment, the flue gas analyser 114 can include one, or more, further gas detectors (not shown) with each further gas detector configured to detect other gases within the flue gas. In the preferred embodiment, the first and the second gas detectors 116, 118 are used to detect an amount of two different gases within the flue gas 110. The first gas detector 116 is preferably configured to detect an amount of oxygen ($O_2$) within the flue gas 110. The second gas detector 118 is preferably configured to detect an amount of carbon dioxide ($CO_2$) within the flue gas 110. In further embodiments, further gas detectors may be used to detect the proportion of other gases in the flue gas 110. Such gases may include nitrogen ($N_2$), carbon monoxide (CO), and hydrogen ($H_2$).

In the preferred embodiment, the flue gas analyser 114 is a portable device and the gas detectors 116, 118 are physically contained within the housing (not shown) of the flue gas analyser 114. In order to measure the efficiency of the burner 108, the flue gas analyser 114 is placed substantially within the flue 112 in order for the gas detectors 116, 118 to measure the proportion of a first gas and a second gas within the flue gas 110.

Alternatively, flue gas may be sucked from the flue down a sample line, passed over sensors 116 and 118 then either exhausted or returned to the flue. In such an embodiment, the gas detectors are connected via a wired or a wireless connection to the flue gas analyser 114. In such an embodiment, the main housing (not shown) of the flue gas analyser 114 may remain substantially outside of the flue 112, and the gas detectors 116, 118 are placed within the flue 110 of the boiler 102.

In yet another embodiment, the flue gas analyser 114 may be physically part of the boiler 102. In such an embodiment, the gas detectors 116, 118 are placed permanently within the flue 112 and the flue gas analyser 114 is integrated into the housing of the boiler 102.

The flue gas analyser also includes a processor 120 that is connected to the first gas detector 116 and the second gas detector 118. In the preferred embodiment, the processor is programmed to obtain readings from the gas detectors 116, 118. The processor 120 is further programmed to estimate the efficiency of the burner 108, calculate the composition of the supply gas 104, and adjust the estimated efficiency based on the calculated composition of the supply gas 104. The functionality of the processor 120, and the process of determining the composition and efficiency is further explained below with reference to FIG. 2.

Figure 2:
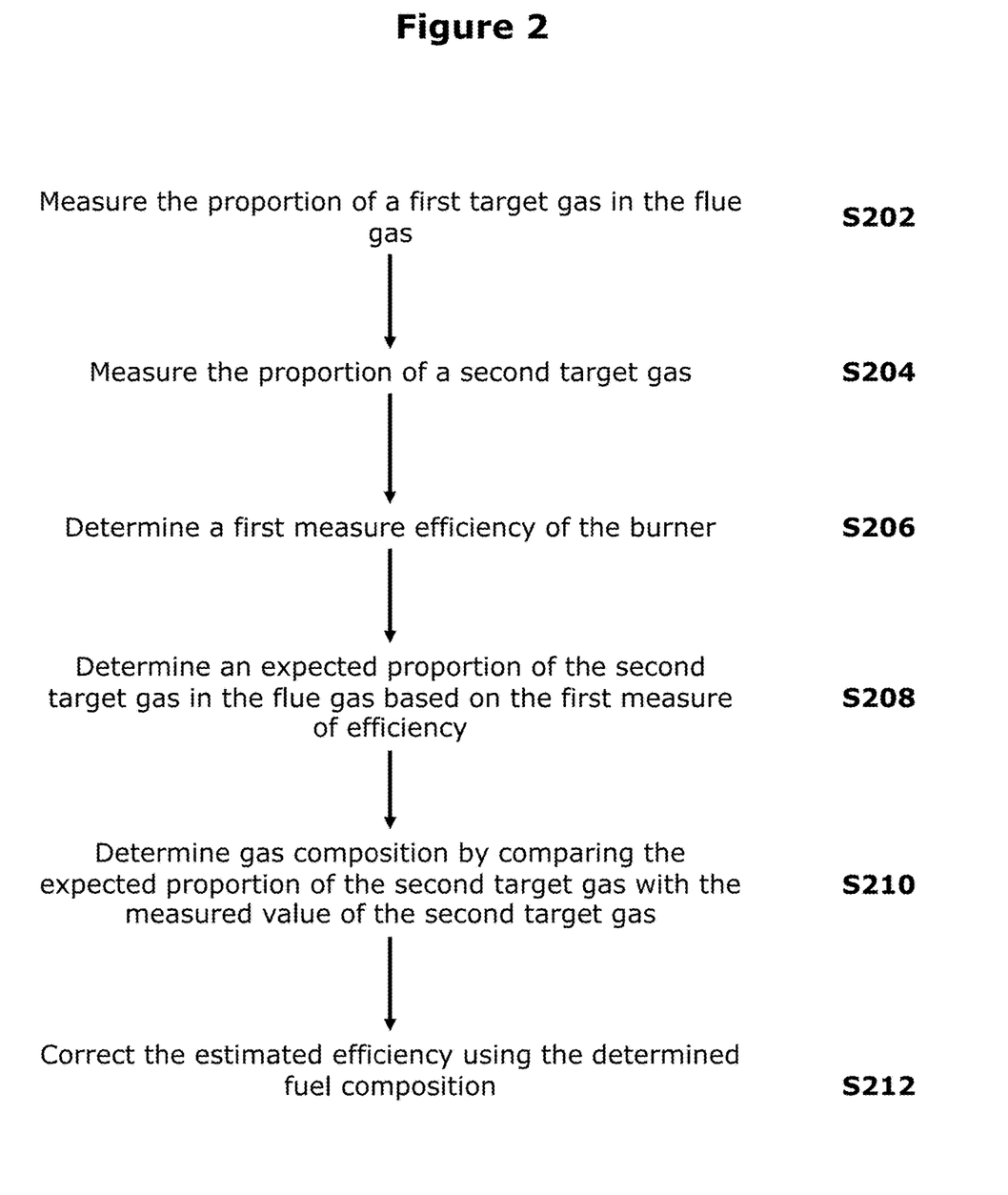
FIG. 2 is a flowchart for analysing flue gas to determine fuel efficiency of a burner.

FIG. 2 shows a flowchart of the steps taken by a flue gas analyser in order to determine the efficiency of a burner according to the preferred embodiment.

As described in brief above, an aspect of various embodiments of the invention is that an accurate estimation of the efficiency of a burner can be obtained by adjusting an estimated efficiency of the burner by determining, and compensating for, the supply gas used. Beneficially, this allows for improvements in the accuracy of the estimated efficiency without requiring the supply fuel type to be known to the flue gas analyser beforehand. Therefore, the flue gas analyser is applicable in a range of settings and in further embodiments the same flue gas analyser can be used for different supply fuel types, such as biogas, butane etc. Furthermore, improvements in the accuracy of the estimated efficiency of a boiler can lead to savings being made by the boiler's owner because inefficient boilers can be identified, repaired, and/or replaced.

In FIG. 2 the steps of the method are present in the manner detailed below for ease of understanding. In further embodiments, the order of the method steps may be changed. For example the measurement of the second target gas may occur sequentially to, or concurrent with, the first target gas. Thus the order of the method steps presented below is non-limiting and may be varied accordingly.

At step S202 of FIG. 2, the proportion of the first target gas present in the flue gas is measured. In the preferred embodiment, the measurement is taken by the first gas detector. The measurement may be provided as a relative quantity of the first gas present in the flue gas. Alternatively, the measurement may be provided as an exact quantity.

In the preferred embodiment, the first target gas measured in the flue gas is oxygen ($O_2$) and the first gas detector is a known sensor configured to detect oxygen. In alternative embodiments, the first target gas may be another gas such as carbon-dioxide ($CO_2$).

The step of measuring the proportion of gas present in the flue gas occurs in a known manner. The measured proportion of the first target gas is provided to the computing means (e.g., computer processor or other suitable processor).

At step S204 the proportion of the second target gas in the flue gas is measured.

In the preferred embodiment, the second target gas is carbon dioxide ($CO_2$) and the second gas detector is configured to detect carbon dioxide. In alternative embodiments, the second target gas may be another gas such as oxygen ($O_2$). The measurement may be provided as a relative quantity of the first gas present in the flue gas. Alternatively, the measurement may be provided as an exact quantity.

At step S206, a first measure of the efficiency of the burner is estimated, wherein the estimate is based on the measurement of the first target gas as measured at S202. In further embodiments the estimate is based on the measurement of the second target gas as measured at S204.

As described below, at step S206 the first measure of the boiler efficiency is made assuming a composition of the fuel. For example the first measure of the boiler efficiency is made assuming a pure methane supply. Based on the assumed fuel composition (e.g. the pure methane supply) a measure of the efficiency of the burner may be made based on the measured value of the first, or second, target gas.

In the preferred embodiment, the efficiency of the burner is calculated by the processor 120 using known combustion analysis. Combustion is the reaction of a fuel with oxygen to produce heat energy and waste products. Combustion analysis measures the gases present in the waste products, i.e. the flue gas, in order to determine the efficiency of the combustion process.

In the preferred embodiment, the efficiency of the burner is determined based on the amount of the first gas detected at step S202 compared with the expected amount of the first gas. The expected amount of the first gas may be found in a number of ways.

In an embodiment, the expected amount of the first gas is given by the assumption that pure methane (CH4) was being used as the supply fuel. If the combustion of the burner is stoichiometric when burning methane, then each molecule of methane reacts with two molecules of oxygen (2O2) and produces one molecule of carbon dioxide (CO2) and two molecules of water (2H2O). Given this, measuring the amount of oxygen (O2) in the flue gas and comparing with the expected amount from a stoichiometric combustion using pure methane provides an initial estimation of the efficiency of the burner.

Alternatively, in order to obtain an expected amount of the first gas when a non-biogas is being combusted, e.g. propane, supply gas profiles may be used. A supply gas profile for a given supply gas comprises information related to the ratio of the proportion of a first gas in the flue gas to the proportion of a second gas in the flue gas, the expected proportion of a first gas in the flue gas, and the expected proportion of a second gas in the flue gas.

The ratio of a first gas to a second gas may be used as the identifier for a given supply gas. In an embodiment, a lookup table is to record the profiles for each supply gas. The lookup table is stored in a memory associated with analyser and accessed by the processor. The lookup table may be queried based on the ratio of a first gas to a second gas. From the supply gas, the expected proportions of gases in the flue gas may be obtained.

Beneficially, this allows for different supply fuel types to be used without the need for the user of the flue gas analyser to manually enter the profile of the supply fuel. This can simplify the operation of the flue gas analyser and reduce the possibility of mistakes being made when information is entered.

Once the first measure of efficiency of the burner has been estimated at step S206, the efficiency can be used at step S208 to predict an expected proportion of the second target gas that should be seen in the flue gas.

Thus at step S208, based on the determined first measure of efficiency of the burner, an expected proportion of the second target gas is determined. The expected proportion of the second target gas being based on the assumed composition of the gas, in the above example a pure methane gas.

In the preferred embodiment, the first target gas is oxygen (O2) and the second target gas is carbon dioxide (CO2). As such, at step S206 the amount of CO2 that should be present in the flue gas is estimated, given the determined first measure of efficiency of the burner, as calculated at step S206.

In the preferred embodiment, the amount of CO2 that should be present in the flue gas is estimated by using the estimated efficiency of the burner, found at step S204, to adjust the amount of CO2 present in the stoichiometric combustion when burning pure methane.

At step S210, the predicted amount of the second target gas, calculated at step S208, is compared with the measured amount of the second target gas, measured at step S204, to obtain a measure of the fuel type. At step S206 an assumption is made regarding the fuel type (for example that the fuel type is 100% methane), and at step S210 the actual composition of the target gas is determined.

The amount of the second target gas measured in the flue gas is expected to be a product of the combustion process and the type of supply gas provided to the combustion process. When burning biogas as the supply gas, different amounts of CO2 may be present in the supply gas and as such may be measured as a component of the flue gas.

Therefore, the proportion of the second target gas in the flue gas, as measured at step S204, may be a product of both combustion and the supply gas type. This is shown pictorially in FIG. 3.

Figure 3:
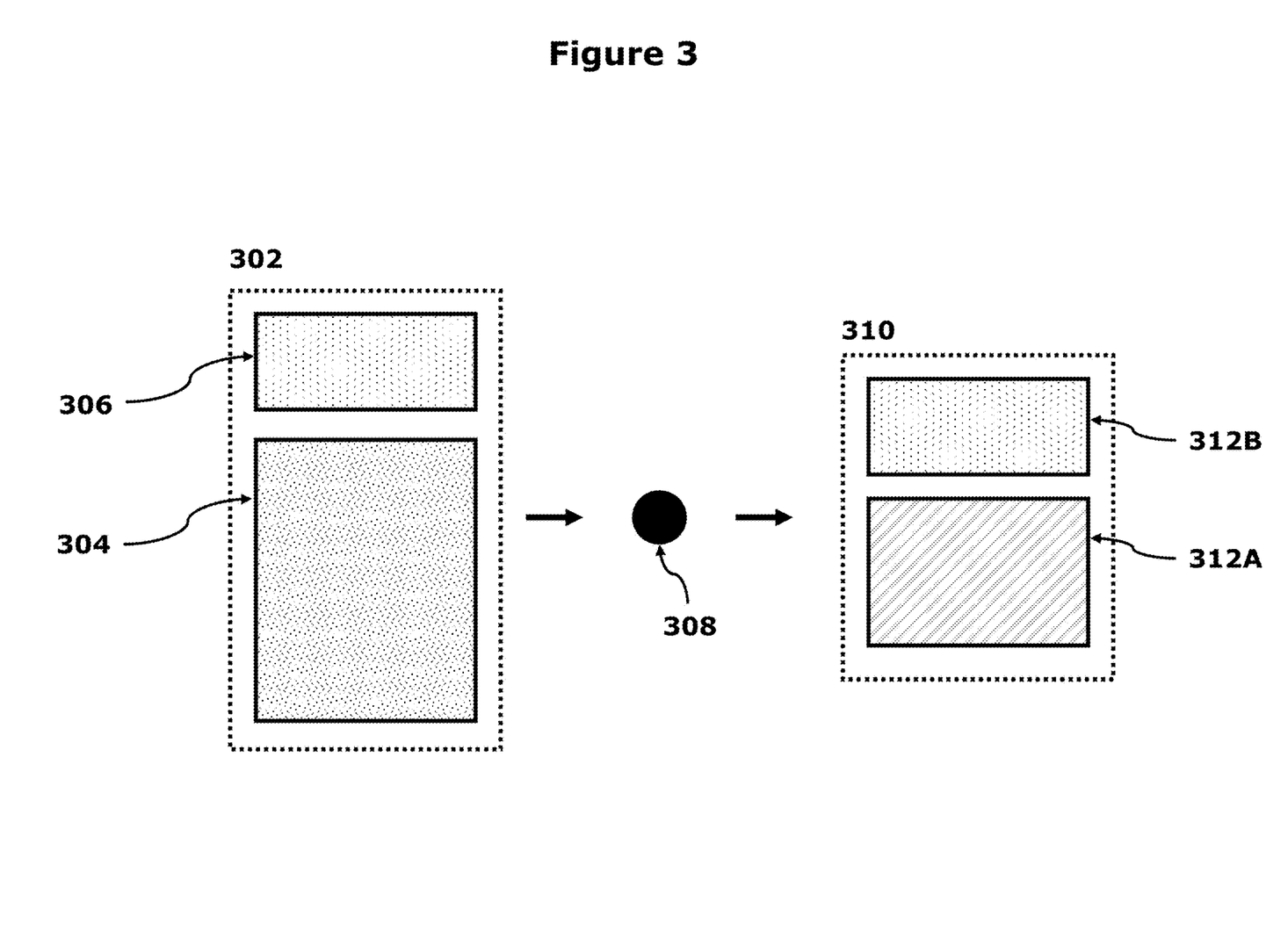
FIG. 3 is a schematic representation of the proportions of a second target gas produced as a result of combustion and the supply gas type.

In FIG. 3 there is shown a supply gas 302 is composed of a proportion of methane (CH4) 304, and an unknown proportion of carbon dioxide (CO2) 306. When the supply gas 302 is combusted 308, an amount of carbon dioxide is produced 310. This is measured as a single proportion of CO2 but is actually composed of an amount of CO2 as a result of combustion 312A, and an amount of CO2 as a result of CO2 present in the supply gas 312B. 312A is therefore a combustion production. 312B is not a combustion product from combustion within the boiler.

Thus at step S210 by comparing the predicted amount of the second target gas, calculated at step S208, with the measured amount of the second target gas as per step S204, the composition of the fuel type can be determined. In other words, by comparing the predicted amount of the target gas with the actual amount of the target gas, the unknown proportion of the target gas 306, as shown in FIG. 3, a composition of the fuel can be determined. For example, at step S210 it may be determined that the fuel type comprises 90% and 10% CO2.

As mentioned above, in the preferred embodiment, the initial efficiency of the burner is calculated using 100% methane (CH4) as the supply gas. However, when using a biogas as the supply gas, the actual supply gas used may contain a proportion of carbon dioxide (CO2). In an embodiment of the invention the amount of CO2 in the supply gas can be determined by determining the amount of detected CO2 in the flue gas that is present after the amount of CO2 as a result of combustion has been accounted for (step S210). In further embodiments different fuel types and gases are used, but the principle remains the same.

Once the amount of CO2 in the flue gas that is a result of combustion has been determined, the remaining amount of CO2 detected in the flue gas can be determined as being the amount of CO2 present with methane (CH4) in the original supply gas.

This residual amount of carbon dioxide (CO2) can be used to determine the composition of the supply gas. In the preferred embodiment, the composition of the supply gas is determined by starting from a supply gas that is 100% methane (CH4). The expected proportion of methane in the supply gas is then decreased based on the residual amount of carbon dioxide detected in the flue gas.

At step S212, the estimated efficiency of the burner, as determined at step S206 is corrected based on the estimated fuel composition as found in step S210.

In the preferred embodiment, the estimated efficiency is recalculated by calculating the combustion efficiency when using a fuel having the composition as per step S210. In an embodiment this would be the fuel having a set percentage of methane. For example, if step S210 determined that the supply gas comprised 5% carbon dioxide (CO2), then step S212 would calculate combustion efficiency of the burner when burning 95% methane (CH4).

In alternative embodiments, the corrected efficiency found at S212 is determined by directly adjusting the first determined efficiency calculated at step S204. For example, if step S210 determined that the supply gas comprised 5% carbon dioxide (CO2), the step S214 would adjust the efficiency estimated at step S204 by multiplying by a factor to compensate for the change in fuel composition.

As such various embodiments of the invention provide a methodology for dealing with the variations in the composition of the fuel supplied to a burner. By measuring the quantities of two separate gases (for example oxygen and carbon dioxide), calculating a boiler efficiency based on a measure of the first gas, and an assumed gas composition burned in the burner, an expected measure of the second gas can be derived. This expected measure of the second gas is then compared with the actual measurement of the second gas, and the offset between the expected measurement and actual measurement will give a measure of the composition of the gas. Using the determined composition of the gas the boiler efficiency can be corrected, or determined, based on the composition of the gas. Thus the variations in composition of the gas can be accounted for, thereby increasing the accuracy of the measurement.

Whilst the above process has been described with a knowledge of the fuel type (e.g. biogas) the above process can be used when there is no knowledge of the fuel type. Different fuel types have different gas ratios when they are burnt. For example butane will have a carbon to hydrogen (C to H) ratio of approximate 4:10. In contrast methane will have a C to H ratio of 1:4. Similarly other types of fuel will display different C to H ratios. The differences in the C to H ratios due to fuel types is much larger than the variations that are seen due to differences in the composition of the gas. Thus after the measurement of the first and second gases (i.e. after step S204) it is possible to, based on the measured gas ratios, to determine the fuel type and based on the knowledge of the fuel type, determine the composition of the fuel.

Thus the above process can provided a measure of efficiency even when the fuel type is unknown.

In a further example, the gas supply may be 90% CH4 and 10% H2 (hydrogen). This is another type of "green fuel". The comparison method for carbon dioxide expected in the exhaust versus actual measured CO2, as described above, is used to estimate the proportion of hydrogen in the fuel and to correct the determination of the efficiency of the burner based on the determined fuel composition.

What is claimed is:

1. A flue gas analyser for determining the efficiency of a burner burning a supply gas and producing a flue gas, comprising:
    a first gas detector, configured to detect an amount of a first target gas in the flue gas;
    a second gas detector, configured to detect an amount of a second different target gas in the flue gas; and
    a processing means;
    wherein the processing means is configured to:
    calculate an efficiency of the burner based on the detected amount of the first target gas in the flue gas and an expected amount of the first target gas in the flue gas;
    predict an amount of the second target gas in the flue gas based on the efficiency of the burner;
    estimate a composition of the supply gas based on the detected amount of the second target gas in the flue gas and the predicted amount of the second target gas in the flue gas; and
    correct the calculated efficiency of the burner based on the estimated composition of the supply gas.

2. The flue gas analyser of claim 1, wherein the processor is further configured to determine the expected amount of the first target gas in the flue gas using a supply gas profile of the supply gas.

3. The flue gas analyser of claim 2, wherein the flue gas analyser is associated with one or more data structures comprising information on a supply gas profile for at least one of a number of supply gases.

4. The flue gas analyser of claim 3, wherein the processor is further configured to obtain the supply gas profile of the supply gas by matching the ratio value of the detected amount of the first target gas in the flue gas with respect to the detected amount of the second target gas in the flue gas to a corresponding ratio value in the supply gas profile in the one or one or more data structures comprising information on the supply gas profile.

5. The flue gas analyser of claim 2, wherein the supply gas profile comprises a ratio value for one of an at least one of a number of supply gases, wherein the ratio value is a ratio of an amount of a first target gas with respect to an amount of a second target gas.

6. The flue gas analyser of claim 5, wherein the supply gas profile comprises an expected amount of a first target gas.

7. The flue gas analyser of claim 6, wherein the supply gas profile further comprises an expected amount of a second target gas.

8. The flue gas analyser of claim 1, wherein the supply gas is a biogas comprising a mixture of carbon dioxide ($CO_2$) and methane ($MH_4$).

9. The flue gas analyser of claim 1, wherein the supply gas is a mixture of methane ($CH_4$) and hydrogen (H).

10. The flue gas analyser of claim 1, wherein the first target gas is oxygen ($O_2$) and the first target gas detector is configured to detect oxygen ($O_2$).

11. The flue gas analyser of claim 1, wherein the second target gas is carbon dioxide ($CO_2$) and the second target gas detector is configured to detect carbon dioxide ($CO_2$).

12. The flue gas analyser of claim 1, wherein the flue gas analyser comprises a power source configured to connect to power one or more of the processor, first target gas detector, and second target gas detector.

13. The flue gas analyser of claim 1, wherein the processing means is a computer processor.

14. A method of using a flue gas analyser to determine the efficiency of a burner burning a supply gas and producing a flue gas, the method comprising using the flue gas analyser to execute the steps of:
    measuring an amount of a first target gas in the flue gas;
    estimating an efficiency of the burner based on an expected amount of the first target gas in the flue gas and the measured amount of the first target gas in the flue gas;
    adjusting the estimated efficiency of the burner;
    wherein the adjusting comprises the steps of:
    predicting an amount of a second target gas in the flue gas using the estimated efficiency of the burner;
    measuring an amount of the second target gas in the flue gas;
    comparing the predicted amount of the second target gas in the flue gas with the measured amount of the second target gas in the flue gas to obtain a correction factor for the second target gas in the flue gas;
    determining a predicted fuel composition of the supply gas using the correction factor for the second target gas in the flue gas; and
    correcting the estimated efficiency of the burner using the predicted fuel composition of the supply gas.

15. The method of claim 14, wherein the expected amount of the first target gas in the flue gas is obtained from a supply gas profile.

16. The method of claim 15, wherein the method comprises determining the supply gas profile by using the flue gas analyser to:
    measure an amount of a first target gas in the flue gas;
    measure an amount of a second target gas in the flue gas;

calculate a flue gas ratio as the ratio of the measured amount of the first target gas in the flue gas to the measured amount of the second target gas in the flue gas;

obtain from a lookup table a supply gas profile based on the flue gas ratio.

17. A flue gas analyser system, comprising:

a supply connector, configured to connect to a supply gas;

a burner, connected to the supply connector and configured to burn the supply gas and produce a flue gas;

a flue element, connected to the burner and configured to convey the flue gas of the burner; and a flue gas analyser, wherein the first gas detector and the second gas detector are positioned such that they detect a first target gas in the flue gas conveyed in the flue element and a second target gas in the flue gas conveyed in the flue element, and wherein the flue gas analyser is configured for determining the efficiency of a burner burning a supply gas and producing a flue gas, and comprises:

a first gas detector, configured to detect an amount of a first target gas in the flue gas;

a second gas detector, configured to detect an amount of a second different target gas in the flue gas; and a processor, wherein the processor is configured to:

calculate an efficiency of the burner based on the detected amount of the first target gas in the flue gas and an expected amount of the first target gas in the flue gas;

predict an amount of the second target gas in the flue gas based on the efficiency of the burner;

estimate a composition of the supply gas based on the detected amount of the second target gas in the flue gas and the predicted amount of the second target gas in the flue gas; and correct the calculated efficiency of the burner based on the estimated composition of the supply gas.

\* \* \* \* \*